United States Patent [19]
Koshino et al.

[11] Patent Number: 5,221,780
[45] Date of Patent: Jun. 22, 1993

[54] 1-(2,6-DIMETHYLPHENYLOXY)-2-ALKANOLS AND PERFUME COMPOSITIONS CONTAINING THE SAME

[75] Inventors: Junji Koshino, Naga; Nao Toi, Sakura; Katsuhiko Tajima, Chiba; Yoshiaki Fujikura, Utsunomiya, all of Japan

[73] Assignee: KAO Corporation, Tokyo, Japan

[21] Appl. No.: 955,337

[22] Filed: Oct. 1, 1992

[30] Foreign Application Priority Data

Oct. 11, 1991 [JP] Japan .................... 3-263731

[51] Int. Cl.$^5$ .............................................. A61K 7/46
[52] U.S. Cl. ......................................... 512/20; 568/648
[58] Field of Search .......................... 512/20; 568/648

[56] References Cited

U.S. PATENT DOCUMENTS

| | | | |
|---|---|---|---|
| 3,382,284 | 5/1968 | Schulze | 568/648 |
| 4,339,612 | 7/1982 | Kranz et al. | 568/648 |
| 4,404,407 | 9/1983 | Harris | 568/648 |
| 4,521,634 | 6/1985 | Fujioka et al. | 512/20 |
| 4,689,180 | 8/1987 | DeLuca et al. | |

FOREIGN PATENT DOCUMENTS 58-159453 9/1983 Japan .

OTHER PUBLICATIONS

Kirk Othmer, Encyclopedia of Chemical Technology, Third Edition, vol. 16 (1981), pp. 947–971.

*Primary Examiner*—James H. Reamer
*Attorney, Agent, or Firm*—Oblon, Spivak, McClelland, Maier & Neustadt

[57] ABSTRACT

A 1-(2,6-dimethylphenyloxy)-2-alkanol of formula (1):

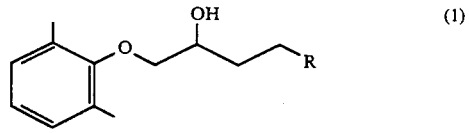

wherein R is an alkyl group having 1 to 4 carbon atoms, and perfume compositions containing the alkanol having an intense woody note, and are useful as fragrance-imparting ingredients for various compositions, particularly in the cosmetic field.

5 Claims, No Drawings

1-(2,6-DIMETHYLPHENYLOXY)-2-ALKANOLS AND PERFUME COMPOSITIONS CONTAINING THE SAME

BACKGROUND OF THE INVENTION

1. Field of the Invention

The present invention relates to a novel fragrance-imparting compound useful for the manufacture of perfumes, and more particularly, to a compound having a strong woody odor, and a perfume composition containing the same.

2. Description of the Background Art

Heretofore, it has generally been known that some alpha-alkoxy-beta-alkanol compounds are useful as a fragrance-imparting material in the manufacture of perfumes. For instance, U.S. Pat. No. 4,689,180 teaches that a compound represented by formula (2) has a woody note.

(2)

Japanese Laid-open patent application (Kokai) No. 9435/1983 describes a compound represented by formula (3) which has a woody or amber note.

(3)

In the case of alpha-phenoxy-beta-alkanols, 2-phenoxy-1-ethanol, having the following formula (4) is known to be useful in the manufacture of perfumes. But 2-phenoxy-1-ethanol is a liquid of practically no odor, as described in "Koryo-no-Jiten" (roughly translated as "Cyclopedia of Perfumes", edited by Fujimaki et al, Asakura Shoten (1980), page 375). Accordingly, this compound is not used as a fragrance-imparting substance, but used as a diluent or a fixative in the manufacture of perfumes.

(4)

As is understood from the relationship between the chemical structures above and their corresponding odors (or lack thereof), slight differences in the chemical structures of these compounds result in greatly different odors. Therefore, in order to obtain a novel fragrance, a number of compounds must be synthesized and examined with respect to the characteristics of each of their odors.

SUMMARY OF THE INVENTION

Accordingly, one object of the present invention is to provide a novel fragrance-imparting compound useful as an ingredient for blending perfumes.

Another object of the present invention is to provide a perfume composition comprising the novel fragrance-imparting compound.

Briefly, these and other objects of the present invention which will become apparent during the following description of the preferred embodiments are attained by a 1-(2,6-dimethylphenyloxy)-2-alkanol of formula (1):

(1)

wherein R is an alkyl group having 1 to 4 carbon atoms.

In accordance with another aspect of this invention, a perfume composition is provided which comprises a 1(2,6-dimethylphenyloxy)-2-alkanol described above.

DETAILED DESCRIPTION OF THE INVENTION AND PREFERRED EMBODIMENTS

Alpha-phenoxy-beta-alkanols are obtainable as a reaction product of phenols and epoxides in a high yield under mild reaction conditions. The present inventors thus synthesized various alpha-phenoxy-beta-alkanol derivatives, and examined their odors. Compounds obtained from the reaction between 2,6-dimethylphenol and expoxides of the formula (6) below have a strong woody odor. Therefore, these compounds are useful as an ingredient for blending perfumes.

In formula (1) above, examples of R include methyl, ethyl, n-propyl, isopropyl, n-butyl, isobutyl and tertbutyl.

The present compounds of formula (1) can be prepared, for example, by the following reaction scheme:

(5) (6)

(1)

wherein R is an alkyl group of from 1 to 4 carbon atoms.

Preferably, 2,6-dimethylphenol (5) is reacted with epoxide (6) in the presence of a base catalyst to obtain the target 1-(2,6-dimethylphenyloxy)-2-alkanol (1).

Reaction media which are useful in this epoxide addition reaction include alcohols such as methanol, ethanol, n-propanol, isopropanol and the like; ethers such as diethyl ether, dibutyl ether, tetrahydrofuran and the like; and hydrocarbons such as hexane, benzene, toluene, xylene and the like. The reaction used to produce the compounds of the present invention, however, can also be conducted without any reaction media (e.g., without solvent, without catalyst, or without both, etc.).

Bases suitable for the process used to produce the present compounds include alkali metal hydroxides such as sodium hydroxide, lithium hydroxide, potassium hydroxide and the like; and carbonates of alkali metals such as sodium carbonate, lithium carbonate, potassium carbonate and the like. Catalysts can be used in powder form, as solid pellets or as an aqueous solution. The amount of base catalyst used in the reaction ranges from 0.01 to 2.0 equivalents per equivalent of compound (5), preferably 0.05 to 0.5 equivalents of base per molar equivalent of the compound of formula (5). The preferred amount of eposide (6) is in a range of from 1.0 to 5.0 molar equivalents, and imparticular, 1.0 to 1.2 molar equivalents per equivalent of compound (5). The reaction is carried out at a temperature of 30 to 200° C., preferably at 50 to 150° C.

Odors of typical compounds among compounds (1) according to the present invention are shown in Table 1 below.

TABLE 1

| Compounds of the Invention | Odor |
| --- | --- |
| [structure: 2,6-dimethylphenyl ether of 2-pentanol] | Strong woody note |
| [structure: 2,6-dimethylphenyl ether of 2-hexanol] | Woody note |

Excellent perfume compositions can be prepared by blending the present compound (1) with other perfume ingredients. The amount of compound (1) blended into perfume compositions varies depending on other compounded perfume ingredients, intended scents and the like, and is not limited provided that a woody odor can be imparted. However, preferably, perfume compositions comprise form 0.01 to 99% by weight of the compound of formula (1), particularly preferably from 0.1 to 40 wt. %, and most preferably, from 0.1 to 20 wt. %.

The compounds according to the present invention have a woody note, and can be prepared by using inexpensive materials, in a high yield and with ease. Accordingly, perfume compositions containing compounds of this invention have a wide utility in the manufacture of perfumes, soaps, shampoos, rinses, detergents, cosmetics, spray articles, fragrances and so on which require vesting of odor.

The present compounds can also be used to improve a conventional perfume composition. Typically, a compound of the present invention is added to or blended with conventional perfume composition. Generally, materials used in conventional perfume compositions include essential oils, concretes, absolutes, resinoids and tinctures. These materials and the corresponding methods of their production are known in the perfumery art. Essential oils are volatile materials obtained from odorous plants by, for example, water extraction, steam distillation, expressing, etc. Concretes are the products of extractions of vegetable matter with hydrocarbon solvents. Absolutes are the alcohol-soluble portions of concretes. Resinoids are the products of extractions of resinous vegetable matter with hydrocarbon solvents. Tinctures are alcoholic solutions obtained by maceration of animal or plant materials with alcohols.

More specifically, the ingredients or components used conventionally in perfume compositions include linalool, terpineol, benzyl acetate, geraniol, pheynylethyl alcohol, hexyl cinnamic aldehyde, phenylacetaldehyde glyceryl acetal, phenylethyl dimethylcarbinol, p-tert-butyl-2-methylhydrocinnamic aldehyde, 4-(4-hydroxy-4-methylpentyl)-3-cyclohexene-1carboxyaldehyde, benzoin Siam, benzoin Sumatra, vanillin, benzoic acid, cinammic acid, castoreum, civet, civetone, clove leaf oil, eugenol, galbanum gum, jasmine concrete, jasmine absolute, labdanum, amber, vegetable amber, maté resinoid, maté absolute, melilot, coumarin and derivatives thereof, mimosa concrete, mimosa absolute, musk tonquin, muscone, myrrh, oakmoss concrete, oakmoss absolute, mousse d,arbre concrete, mousse d'arbre absolute, olibanum, opopanax, ylang-ylang, rose, orris, patchouli, rosemary oil, sandalwood oil, vetivert oil, acetylated vetiver oil, violet leaf concrete, violet leaf absolute, and chemicals including norpatchoulenol, β-damascenone, methyl jasmonate, methyl dihydrojasmonate, α-pinene derivatives such as α-terpineol and isobornyl acetate, higher aliphatic alcohols (e.g., those of from 8 to 30 carbon atoms), benzaldehyde, cinnamaldehyde, cinnamyl alcohol, indole, salicylic acid, acetylated cedarwood terpenes, amyl cinnamic aldehyde, amyl salicylate, benzyl salicylate, p-tert-butylcyclohexyl acetate, citronellol, galaxolide, geraniol, hedione, linalyl acetate, γ-methylionones, musk ambrette, tetrahydromuguol, terpinyl acetate, and mixtures thereof. The above components may also be mixed or blended with suitable carriers, such as water, lower alcohols ($C_1$–$C_6$ alcohols), low molecular weight esters ($C_1$–$C_6$ alcohols of $C_1$–$C_6$ acids), and phthalic acid esters (for example, dimethyl phthalate and/or diethyl phthalate, etc.).

Having now generally described this invention, a further understanding can be obtained by reference to certain specific examples which are provided herein for purposes of illustration only, and are not intended to be limiting, unless otherwise specified.

Example 1: Synthesis of
1-(2,6-dimethylphenyloxy)-2-pentanol 2,6-Dimethylphenol (122 g, 1.00 mol) and an aqueous 20% sodium hydroxide solution (25 g) were placed in a 500 ml round bottom flask equipped with a Dimroth condenser and a dropping funnel while passing nitrogen gas through the reaction vessel. The mixture was heated to 80° C. To this solution, 90.3 g (1.05 mol) of 1,2-pentenoxide was added dropwise over about 2 hours, and the reaction was stirred at 80° C. for 6 additional hours. The reaction mixture was cooled, and the organic layer was separated from the lower aqueous layer of sodium hydroxide solution. The organic phase was distilled and the fraction at boiling point (B.P.) 138° -140° C. (4 mm Hg) was collected. Yield: 198 g of 1-(2,6-dimethylphenyloxy)-2-pentanol (B.P. 138° -140° C./4 mmHg; 95%).

IR (film, $cm^{-1}$): 765, 1011, 1092, 1137, 1200, 1263, 1377, 1476, 2866, 2926, 2956, 3448

NMR (200 MHz, $CDCl_3$, ppm): 0.96 (t, J=7Hz, 3H), 1.3–1.7 (m, 4H), 1.8–2.2 (m, 1H), 2.32 (s, 6H), 3.6–3.8 (m, 2H), 3.9–4.2 (m, 1H),
6.9–7.2 (m, 3H)

Example 2: Synthesis of
1-(2,6-dimethylphenyloxy)-2-hexanol

The process of Example 1 was followed, using 105 g (1.05 mol) of 1,2-hexene oxide in place of 90.3 g of 1,2pentenoxide. Yield: 206 g of 1-(2,6-dimethylphenyloxy)-2-hexanol (B.P.: 149°-150° C./4 mmHg; 93%).

IR (film, cm$^{-1}$): 765, 1017, 1089, 1200, 1263, 1377 1473, 2860, 2926, 2956, 3448

NMR (200 MHz, CDCl$_3$, ppm): 0.93 (t, J=7Hz, 3H), 1.1-1.8 (m, 6H), 2.0-2.5 (m, 1H), 2.29 (s, 6H), 3.6-3.9 (m, 2H), 3.9-4.2 (m, 1H), 6.9-7.2 (m, 3H)

Example 3: Perfume composition of muguet note

The following components were combined in the amounts recited in the Table below:

|  | (Parts by weight) |
| --- | --- |
| Linalool | 50 |
| Terpineol | 50 |
| Benzyl acetate | 50 |
| Geraniol | 50 |
| Phenylethyl alcohol | 150 |
| Lilial[1] | 100 |
| Lyral[2] | 200 |
| Hexyl cinnamic aldehyde | 150 |
| Phenylacetaldehyde glyceryl acetal | 50 |
| Phenylethyl dimethylcarbinol | 50 |
|  | 900 |

[1]Lilial: Obtained from Givaudan S.A.; p-tert-butyl-2-methylhydrocinnamic aldehyde.
[2]Lyral: Obtained from IFF Inc.; 4-(4-hydroxy-4-methyl-pentyl)-3-cyclohexene-1-carboxyaldehyde.

A perfume composition of muguet note with a characteristic fresh floral impression was obtained by adding 100 parts by weight of 1-(2,6-dimethylphenyloxy)-2-pentanol to 900 parts by weight of the above formulation.

Obviously, numerous modifications and variations of the present invention are possible in light of the above teachings. It is therefore to be understood that within the scope of the appended claims, the invention may be practiced otherwise than as specifically described herein.

What is claimed is:

1. A 1-(2,6-dimethylphenyloxy)-2-alkanol of formula (1)

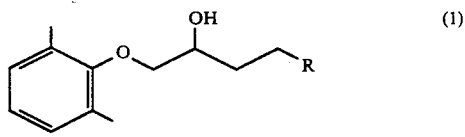

wherein R is an alkyl group having 1 to 4 carbon atoms.

2. A perfume composition, the improvement wherein the composition further comprises the 1-(2,6-dimethylphenyloxy)-2-alkanol of claim 1.

3. The perfume composition of claim 2, wherein said alkanol is present in an amount of from 0.01 to 99% by weight of the composition.

4. The perfume composition of claim 3, wherein said alkanol is present in an amount of from 0.01 to 40% by weight of the composition.

5. The perfume composition of claim 4, wherein said alkanol is present in an amount of from 1.0 to 20% by weight of the composition.

* * * * *